United States Patent
Westlund et al.

(10) Patent No.: US 7,657,324 B2
(45) Date of Patent: *Feb. 2, 2010

(54) SEAL FOR USE WITH CARDIAC LEAD

(75) Inventors: Randy Westlund, Minneapolis, MN (US); Bruce Tockman, Scandia, MN (US); Gwen Crevensten, Minneapolis, MN (US); Lili Liu, White Bear Lake, MN (US); Christopher M. Zerby, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 829 days.

This patent is subject to a terminal disclaimer.

(21) Appl. No.: 10/617,881

(22) Filed: Jul. 14, 2003

(65) Prior Publication Data

US 2005/0090883 A1    Apr. 28, 2005

Related U.S. Application Data (60) Continuation of application No. 09/738,590, filed on Dec. 15, 2000, now Pat. No. 6,634,364, and a continuation-in-part of application No. 09/970,195, filed on Oct. 2, 2001, now Pat. No. 6,901,288, which is a continuation of application No. 09/579,765, filed on May 26, 2000, now abandoned, which is a division of application No. 09/133,310, filed on Aug. 12, 1998, now Pat. No. 6,240,321.

(51) Int. Cl.
*A61N 1/05* (2006.01)

(52) U.S. Cl. .................................. 607/122; 600/374

(58) Field of Classification Search ............... 607/116, 607/122, 123; 600/373, 374, 377, 585; 128/899; 604/167.01, 167.02, 336
See application file for complete search history.

(56) References Cited

U.S. PATENT DOCUMENTS

| 3,769,984 | A | 11/1973 | Muench |
| 4,011,875 | A | 3/1977 | Lehr et al. |
| 4,106,512 | A | 8/1978 | Bisping |

(Continued)

FOREIGN PATENT DOCUMENTS

CA    2178934    4/1996

(Continued)

OTHER PUBLICATIONS

Advances in Pacemaker Technology (M. Schaldach et al. eds., Springer-Verlag, 1975) pp. 30-31.

(Continued)

*Primary Examiner*—Kennedy J Schaetzle
(74) *Attorney, Agent, or Firm*—Finnegan, Henderson, Farabow, Garrett & Dunner (57) ABSTRACT

A seal adapted for use with medical devices is provided. The medical device may be a lead having a distal tip adapted for implantation on or about the heart and for connection to a system for monitoring or stimulating cardiac activity. The lead assembly in one embodiment includes an atraumatic tip. A seal is provided within the lead tip assembly, which prevents or limits further entry of fluids through the lead tip. The lead may be a left ventricular lead with a hemostasis mechanism provided therewithin.

16 Claims, 7 Drawing Sheets

U.S. PATENT DOCUMENTS

| | | |
|---|---|---|
| 4,146,036 A | 3/1979 | Dutcher et al. |
| 4,185,639 A | 1/1980 | Linder |
| 4,217,913 A | 8/1980 | Dutcher |
| 4,282,885 A | 8/1981 | Bisping |
| 4,311,153 A | 1/1982 | Smits |
| 4,355,646 A | 10/1982 | Kallok et al. |
| 4,467,806 A | 8/1984 | Bhiwandiwala et al. |
| 4,506,680 A | 3/1985 | Stokes |
| 4,537,186 A | 8/1985 | Verschoof et al. |
| 4,577,642 A | 3/1986 | Stokes |
| 4,649,904 A | 3/1987 | Krauter et al. |
| 4,649,938 A | 3/1987 | McArthur |
| 4,667,686 A | 5/1987 | Peers-Travarton |
| 4,819,661 A | 4/1989 | Heil, Jr. et al. |
| 4,886,074 A | 12/1989 | Bisping |
| 4,932,407 A | 6/1990 | Williams |
| 4,934,381 A | 6/1990 | MacGregor |
| 4,943,289 A | 7/1990 | Goode et al. |
| 4,953,564 A | 9/1990 | Berthelsen |
| 5,002,067 A | 3/1991 | Berthelsen et al. |
| 5,003,990 A | 4/1991 | Osypka |
| 5,003,992 A | 4/1991 | Holleman et al. |
| 5,011,482 A | 4/1991 | Goode et al. |
| 5,013,310 A | 5/1991 | Goode et al. |
| 5,014,696 A | 5/1991 | Mehra |
| 5,015,238 A | 5/1991 | Solomon et al. |
| 5,016,646 A | 5/1991 | Gotthardt et al. |
| 5,041,107 A | 8/1991 | Heil, Jr. |
| 5,099,838 A | 3/1992 | Bardy |
| 5,103,837 A | 4/1992 | Weidlich et al. |
| 5,207,683 A | 5/1993 | Goode et al. |
| 5,234,437 A | 8/1993 | Sepetka |
| 5,243,996 A | 9/1993 | Hall |
| 5,266,325 A | 11/1993 | Kuzma et al. |
| 5,283,063 A | 2/1994 | Freeman |
| 5,299,580 A | 4/1994 | Atkinson et al. |
| 5,304,121 A | 4/1994 | Sahatjian |
| 5,304,218 A | 4/1994 | Alferness |
| 5,313,943 A | 5/1994 | Houser et al. |
| 5,324,324 A | 6/1994 | Vachon et al. |
| 5,348,021 A | 9/1994 | Adams et al. |
| 5,350,404 A | 9/1994 | Adams et al. |
| 5,381,790 A | 1/1995 | Kanesaka |
| 5,397,343 A | 3/1995 | Smits |
| 5,425,755 A | 6/1995 | Doan |
| 5,433,729 A | 7/1995 | Adams et al. |
| 5,447,534 A | 9/1995 | Jammet |
| 5,456,708 A | 10/1995 | Doan et al. |
| 5,458,621 A | 10/1995 | White et al. |
| 5,476,498 A | 12/1995 | Ayers |
| 5,476,501 A | 12/1995 | Stewart et al. |
| 5,487,385 A | 1/1996 | Avitall |
| 5,496,360 A | 3/1996 | Hoffmann et al. |
| 5,507,301 A | 4/1996 | Wasicek et al. |
| 5,507,724 A | 4/1996 | Hofmann et al. |
| 5,509,411 A | 4/1996 | Littmann et al. |
| 5,514,173 A | 5/1996 | Rebell et al. |
| 5,520,194 A | 5/1996 | Miyata et al. |
| 5,522,874 A | 6/1996 | Gates |
| 5,531,780 A | 7/1996 | Vachon |
| 5,545,204 A | 8/1996 | Cammilli et al. |
| 5,562,275 A | 10/1996 | Weissenfluh |
| 5,584,873 A | 12/1996 | Shoberg et al. |
| 5,609,622 A | 3/1997 | Soukup et al. |
| 5,620,477 A | 4/1997 | Pless et al. |
| 5,643,231 A | 7/1997 | Lurie et al. |
| 5,669,790 A | 9/1997 | Carson et al. |
| 5,693,034 A | 12/1997 | Buscemi et al. |
| 5,720,631 A | 2/1998 | Carson et al. |
| 5,755,765 A | 5/1998 | Hyde et al. |
| 5,755,766 A | 5/1998 | Chastain et al. |
| 5,782,239 A | 7/1998 | Webster, Jr. |
| 5,782,760 A | 7/1998 | Schaer |
| 5,800,495 A | 9/1998 | Machek et al. |
| 5,800,497 A | 9/1998 | Bakels et al. |
| 5,803,928 A | 9/1998 | Tockman et al. |
| 5,807,384 A | 9/1998 | Mueller |
| 5,897,819 A | 4/1999 | Miyata et al. |
| 5,902,329 A | 5/1999 | Hoffman et al. |
| 5,910,364 A | 6/1999 | Miyata et al. |
| 5,935,137 A | 8/1999 | Saadat et al. |
| 5,935,160 A | 8/1999 | Auricchio et al. |
| 5,951,597 A | 9/1999 | Westlund et al. |
| 5,957,842 A | 9/1999 | Littmann et al. |
| 6,039,685 A | 3/2000 | Bushek |
| 6,042,624 A | 3/2000 | Breyen et al. |
| 6,141,576 A | 10/2000 | Littmann et al. |
| 6,192,280 B1 | 2/2001 | Sommer et al. |
| 6,193,748 B1 | 2/2001 | Thompson et al. |
| 6,240,321 B1 | 5/2001 | Janke et al. |
| 6,287,280 B1 | 9/2001 | Lampropoulos et al. |
| 6,356,791 B1 | 3/2002 | Westlund et al. |
| 6,377,856 B1 | 4/2002 | Carson |
| 6,408,213 B1 | 6/2002 | Bartig et al. |
| 6,447,539 B1 | 9/2002 | Nelson et al. |
| 6,473,651 B1 | 10/2002 | Kuzma et al. |
| 6,634,364 B2 | 10/2003 | Westlund et al. |
| 6,714,823 B1 * | 3/2004 | De Lurgio et al. .......... 607/122 |
| 2002/0193742 A1 | 12/2002 | Davey |

FOREIGN PATENT DOCUMENTS

| | | |
|---|---|---|
| DE | 195 09 609 A1 | 10/1995 |
| DE | 199 16 866 A1 | 10/1999 |
| EP | 0 057 877 B1 | 8/1982 |
| EP | 0 709 111 A2 | 5/1996 |
| EP | 0 709 111 A3 | 11/1997 |
| EP | 0 993 840 | 4/2000 |
| GB | 2 032 278 A | 5/1980 |
| GB | 2268066 | 1/1994 |

OTHER PUBLICATIONS

Research Disclosure, "Guidewire Placement of Electrical Lead," Oct. 1993, p. 685.

DiColo G. et al., "Effect of Water-Soluble Additives on Drug Release From Silicone Rubber Matrices", *Int. J. Pharm.*, vol. 30, 1-7, (May 1986).

Fedors R.F., "Osmotic Effects in Water Absorption by Polymers", *Polymer*, vol. 21, 207-212, (Feb. 1980).

Golomb G. et al., "The Relationship Between Drug Release Rate, Particle Size and Swelling of Silicone Matrices", *Journal of Controlled Release*, vol. 12, 121-132, (1990).

* cited by examiner

SEAL FOR USE WITH CARDIAC LEAD

CROSS REFERENCE TO RELATED APPLICATIONS

This application is a continuation application of U.S. application Ser. No. 09/738,590, filed Dec. 15, 2000, now issued as U.S. Pat. No. 6,634,364, and is a Continuation-In-Part Application of U.S. application Ser. No. 09/970,195, filed Oct. 2, 2001, now issued as U.S. Pat. No. 6,901,288, which is a continuation of U.S. application Ser. No. 09/579,765, filed May 26, 2000, now abandoned, which is a divisional of U.S. application Ser. No. 09/133,310, filed on Aug. 12, 1998, now issued as U.S. Pat. No. 6,240,321, the specifications of all of which are incorporated herein by reference.

FIELD OF THE INVENTION

The present invention relates generally to medical devices, such as leads and catheters. More particularly, it pertains to seals or hemostasis mechanisms for medical devices such as leads and catheters.

BACKGROUND OF THE INVENTION

Leads implanted in or about the heart have been used to reverse (i.e., defibrillate or cardiovert) certain life threatening arrhythmias, or to stimulate contraction (pacing) of the heart. Electrical energy is applied to the heart via the leads to return the heart to normal rhythm. Leads have also been used to sense in the atrium or ventricle of the heart and to deliver pacing pulses to the atrium or ventricle. The same lead used to sense the condition is sometimes also used in the process of delivering a corrective pulse or signal from the pulse generator of the pacemaker.

Cardiac pacing may be performed by the transvenous method or by leads implanted directly onto the ventricular epicardium. Most commonly, permanent transvenous pacing is performed using a lead positioned within one or more chambers of the heart. A lead, sometimes referred to as a catheter, may be positioned in the right ventricle or in the right atrium through a subclavian vein, and the lead terminal pins are attached to a pacemaker, which is implanted subcutaneously. The lead may also be positioned in both chambers, depending on the lead, as when a lead passes through the atrium to the ventricle. Pacing and sensing electrodes may be positioned within the atrium or the ventricle of the heart.

Pacemaker leads represent the electrical link between the pulse generator and the heart tissue, which is to be excited. These pacemaker leads include single or multiconductor coils of insulated wire having an insulating sheath. The coils provide a cylindrical envelope, many times referred to as a lumen, which provides a space into which a stiffening stylet or guidewire can be inserted. The conductive coil is connected to an electrode in an electrode assembly at a distal end of the lead.

During use, the lead conducts critical information to and from the heart. The lead, therefore, must remain in sufficient operative condition without interference from entry of bodily fluids. A lumen used as a means for deployment must remain free of blood to remain functional. Clotting blood hampers maneuverability. In addition, blood in the lumen could cause corrosion. To prevent entry of bodily fluids into the lead, a seal can be provided at the distal end of the lead. Conventional leads do not have open ends, i.e. the lumens thereof are closed. Leads which have moving parts, such as retractable fixation parts for example, use O-ring type seals to seal the distal end of the lead from entry of bodily fluids. The O-ring seals can be difficult to manufacture due to dimensional constraints which affect the effectiveness of the seal and the ease with which parts move.

Accordingly, there is a need for a lead, which is sufficiently sealed from the environment. There is also a need for a reliable means for performing cardiac sensing and pacing of the left atrium or ventricle, with a lead which is sufficiently sealed from the environment.

SUMMARY OF THE INVENTION

In one embodiment, a body-implantable lead assembly is provided comprising a lead, one end being adapted to be connected to an electrical supply for providing or receiving electrical pulses. The lead further comprises a distal tip, which is adapted to be atraumatic. The lead also has a sheath of material inert to body materials and fluids and at least one conductor extending through the lead body. The lead has a distal electrode adapted for implantation proximate to or within the heart while connected with a system for monitoring or stimulating cardiac activity. The lead, however, is not limited to use in the coronary vascular system.

In one embodiment a distal tip electrode is provided which is adapted for implantation proximate to the heart, the electrode being connected with a system for monitoring or stimulating cardiac activity.

The lead includes a seal or hemostasis mechanism. The terms "seal", "seal mechanism" and "bemostasis mechanism" may be used interchangeably in describing the present invention. The seal can be in the form of a polymer membrane located at the distal or proximal end of the lead.

In one embodiment, the provided medical device includes an electrode tip, supplies a stylet for placement of the lead, which is sealed from exposure to fluids. The lead avoids deterioration of its function due to entry of liquid inside the lead, owing to the provision of a highly effective seal. In addition, the seal remains functional when the lead is removed for short periods of time from an environment filled or partially filled with fluid.

The present invention provides a lead, which may be positioned in or on the left ventricle to perform cardiac pacing. In one embodiment the present invention contemplates all types of over the wire leads which have an open distal end, which may be positioned in or on the left chambers of the heart for use in sensing and pacing, and/or "shocking" or cardioverting. The present invention is directed to left ventricular leads providing a hemostasis mechanism or seal in the lead lumen. It has been discovered that a left ventricular lead deployed over a guide wire into the coronary venous system is easily maneuvered into a desired pacing site. It has also been discovered that when the vasculature is unusually difficult or the procedure requires more time, blood can migrate into the lead lumen and begin to coagulate. This can cause undue friction between the lead and the guide wire, interfering with the maneuverability of the lead. Accordingly, the present invention provides an over the wire left ventricular lead having a hemostasis mechanism or seal, which preempts blood from entering the lead lumen.

In another embodiment, a hemostasis mechanism for left ventricular leads is provided which comprises a polymer membrane at the proximal or distal end of the lead. The membrane may be a cusp valve made of a suitable biocompatible polymer. In another embodiment, the hemostasis mechanism may be removable and disposable. This embodiment may be removably attached to the terminal pin of the left ventricular lead. In another embodiment, a grommet attachment to the terminal pin in combination with a hemostasis valve which permits the passage of the guide wire and a port for introduction of fluid are provided. The present invention also contemplates the use of the leads and seals disclosed herein as left ventricular leads.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims and their equivalents.

Figure 1:
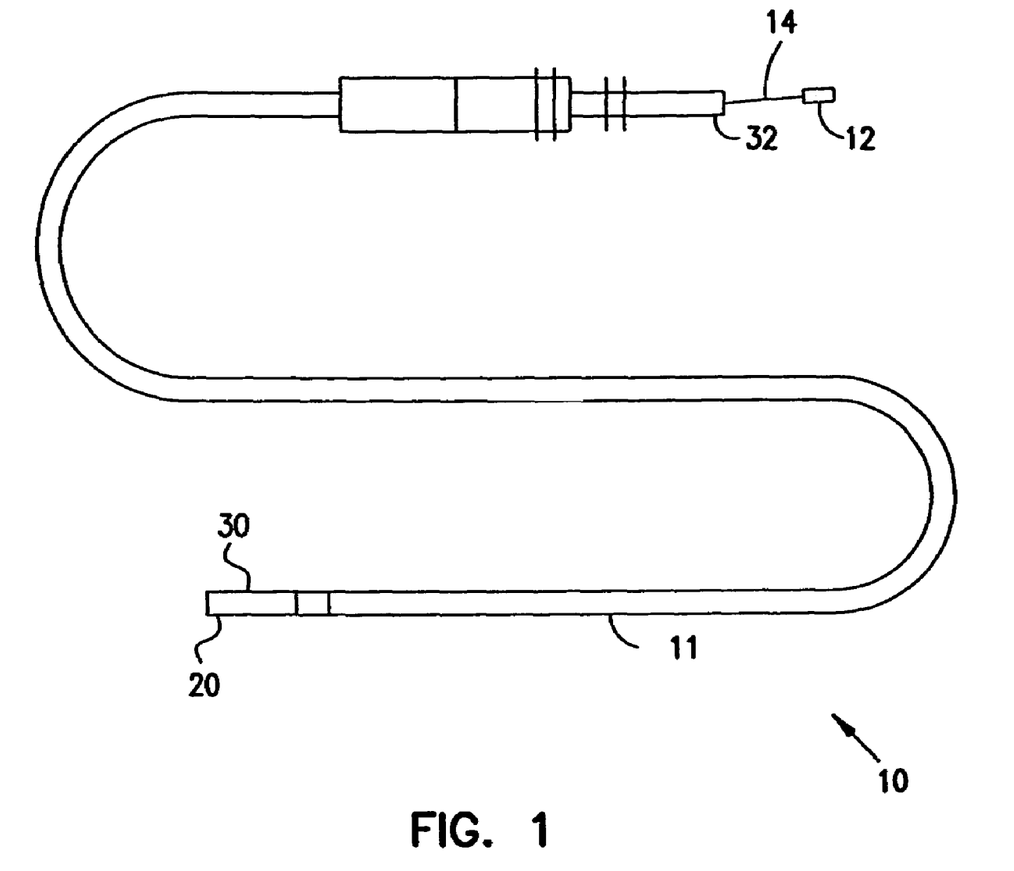
FIG. 1 is a side elevational view illustrating a lead constructed in accordance with one embodiment.

One embodiment of a lead 10 is illustrated in FIG. 1. The lead 10 comprises a lead body 11, and extends from a proximal end 32 to a distal end 30. An elongate conductor is contained within the lead body 11, and a lead tip 20 is disposed within the distal end 30. The lead tip 20 comprises an open lumen lead tip. The stylet 14 stiffens the lead 10, and can be manipulated to introduce an appropriate curvature to the lead 10, facilitating the insertion of the lead 10 into and through a vein and through an intracardiac valve to advance the distal end 30 of the lead 10 into the heart, for example into the right ventricle of the heart. A stylet knob 12 is coupled with the stylet 14 for rotating the stylet 14 and advancing the lead 10.

Figure 2:
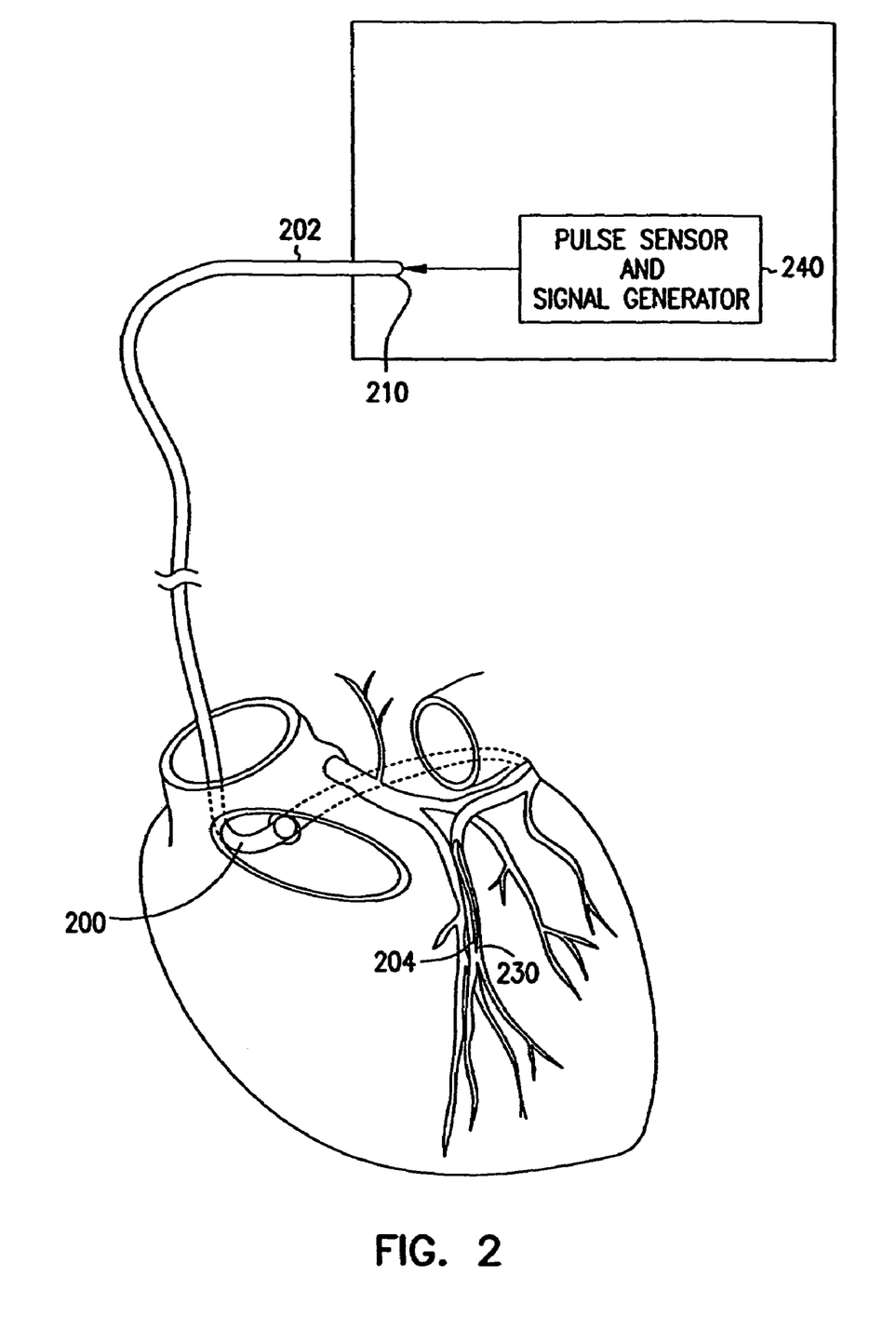
FIG. 2 is a cross-sectional view illustrating a system for delivering signals to the heart constructed in accordance with one embodiment.

FIG. 2 illustrates another embodiment, showing a view of a lead 200 adapted for delivering electrical pulses to stimulate the heart. The lead 200 is not limited to any particular type of lead, but in a preferred embodiment the lead is an open lumen lead, i.e. a lead having a lumen open at its distal end. The lead 200 extends from a proximal end 202, which is adapted to connect with equipment which supplies electrical pulses, to a distal end 204 which is adapted to be inserted into the heart. Proximate to the distal end 204 is an electrode tip 230. The electrode tip 230 includes a seal (FIG. 3A or 3B) disposed therein to preempt bodily fluid from entering through the electrode tip 230.

A connector terminal 210 is disposed near the proximal end 202 of the lead 200. The connector terminal 210 electrically connects the various electrodes and conductors within the lead 200 to a pulse sensor and signal generator 240. The pulse sensor and signal generator 240 contains electronics to sense various electrical signals of the heart and also produce electrical pulses for delivery to the heart, depending on the type of lead 200 used. The pulse sensor and signal generator 240 also contains electronics and software necessary to detect certain types of arrhythmias and to correct for them. The lead terminal connector 210 provides for the electrical connection between the lead 200 and the pulse sensor and signal generator 240.

Referring to FIGS. 3A-3D and 4-6, a hemostasis mechanism for leads, for example left ventricular leads, is shown. The hemostasis mechanism as described herein is used to prevent body fluids from migrating into the lumen of a left ventricular lead during and after deployment into the coronary vascular system. The hemostasis mechanisms described herein apply to sealing the internal lumen of a lead implanted in the heart but are not intended to be limited to that application.

The embodiments illustrated in FIGS. 3A-3D and 4-6 are directed to over the wire left ventricular leads with hemostasis mechanisms to preempt blood from entering the lead lumen, thus maintaining the superior maneuvering capabilities of the over the wire left ventricular lead.

Figure 3A:
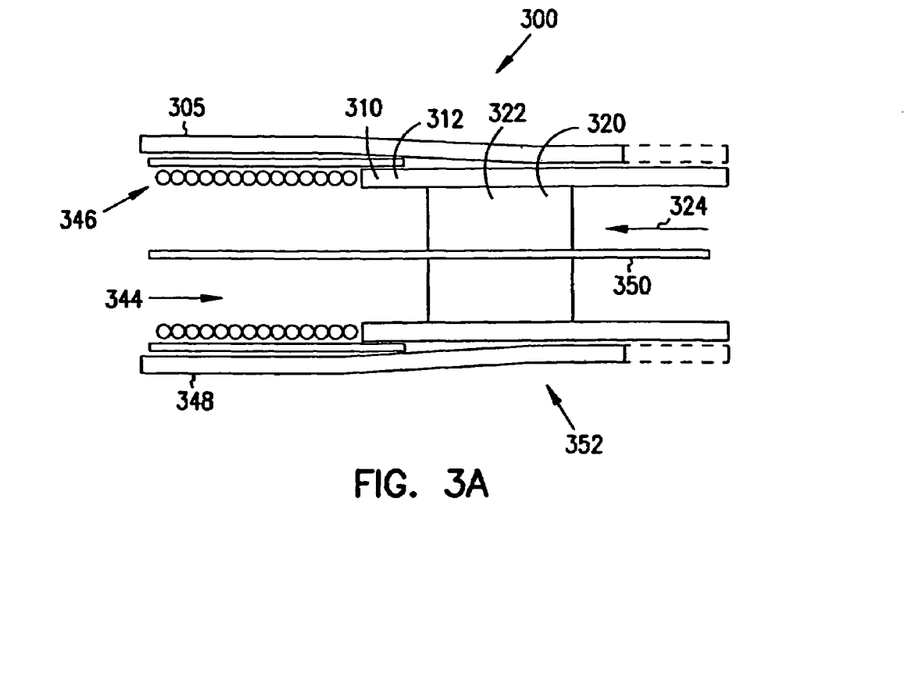
FIG. 3A is a cross-sectional view of the distal portion of an over the wire left ventricular lead for monitoring and stimulating the heart constructed in accordance with one embodiment.

Illustrated in FIG. 3A is a lead 300 wherein a hemostasis mechanism 320 is provided. The lead 300 is adapted to be implanted in, on, or around the heart. The lead 300 can comprise a number of configurations such as, although not limited to, those described above and shown in the Figures, for instance the leads shown in FIGS. 1 and 2. The hemostasis mechanism of the present invention may be utilized with a lead as set forth in U.S. Pat. No. 5,755,766, incorporated herein by reference.

Figure 3B:
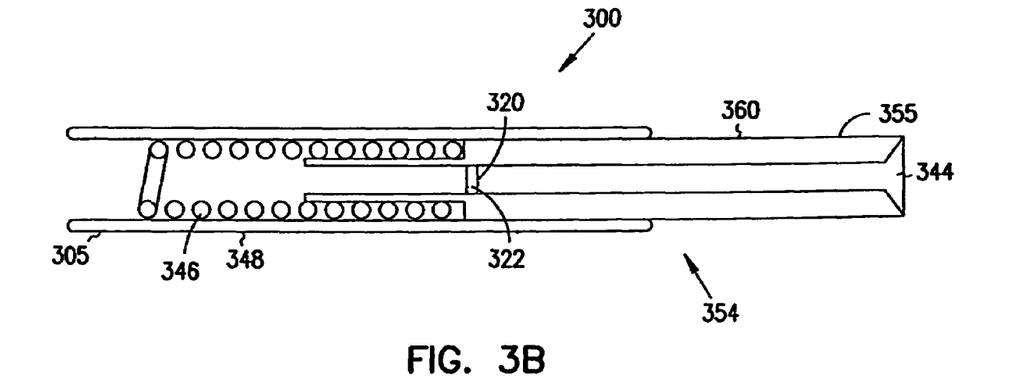
FIG. 3B is a cross-sectional view of the proximal portion of an over the wire left ventricular lead for monitoring and stimulating the heart constructed in accordance with one embodiment.

As shown at FIG. 3A, lead 300 is an over the wire left ventricular lead. Disposed within the lead 300 is a conductor coil 346, which is contained by a lead body 305 having an outer diameter 348. In one embodiment, lead body 305 is made of silicone rubber having an interior layer of polytetrafluoroethylene (PTFE), and conductor coil 346 is made of titanium (Ti). Hemostasis mechanism 320 is located within the lead lumen 344 at or near the distal end 352 of the lead 300. In an alternative embodiment shown at FIG. 3B, hemostasis mechanism 320 is located within the lead lumen 344 at or near the proximal end 354 of the lead 300. Providing a seal at the proximal end puts the point of drag outside the vasculature where it can easily be maneuvered and lubricated as necessary. In a still further embodiment, lead 300 has a first hemostasis mechanism located at or near its distal end 352 (as shown at FIG. 3A), and a second hemostasis mechanism located at or near proximal end 354 (as shown at FIG. 3B).

In one embodiment, hemostasis mechanism 320 comprises a substantially planar membrane. It should be noted that the hemostasis mechanism 320 optionally has other configurations other than planar. In one embodiment, the membrane is normal to the main axis of the lead 300. In one embodiment, the hemostasis mechanism 320 is comprised of a housing 310 having a polymer membrane 322. Housing 310 is made of any suitable biocompatible material. Housing 310 may be made of molded plastic, or a metal such as titanium. The housing may alternatively be made of silicone rubber or polyurethane, or other biocompatible material. The membrane 322 is made of any suitable biocompatible material. Examples of suitable materials include but are not limited to silicone rubber, polyurethane, hydrogels and other biocompatible elastomers.

Figure 3C:
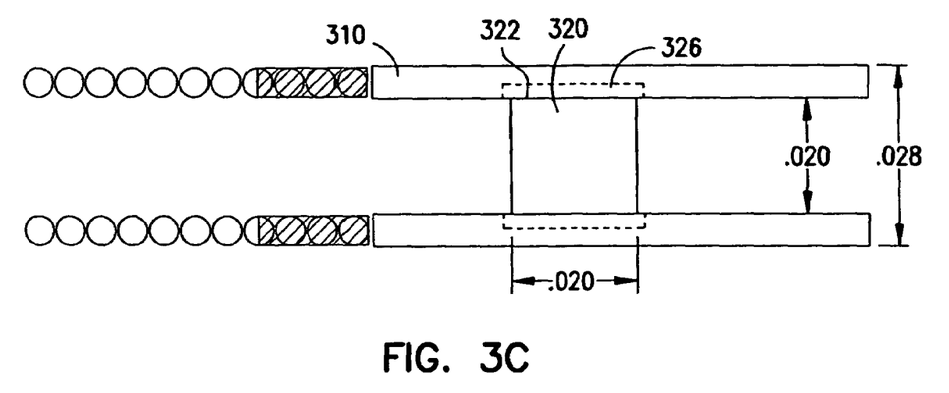
FIG. 3C is a cross-sectional view of the distal portion of an over the wire left ventricular lead for monitoring and stimulating the heart constructed in accordance with one embodiment.
Figure 3D:
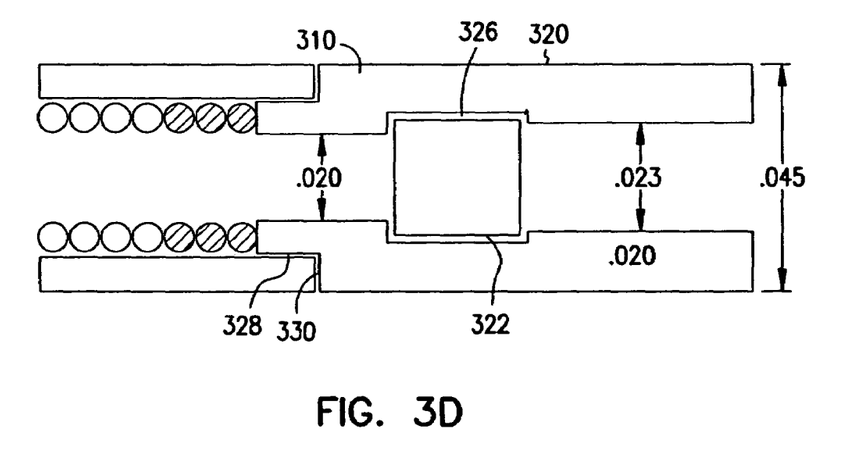
FIG. 3D is a cross-sectional view of the distal portion of an over the wire left ventricular lead for monitoring and stimulating the heart constructed in accordance with one embodiment.

Membrane 322 is held within housing 310, in one option, by an interference fit. Alternatively, membrane 322 is adhesively bonded to housing 310. As shown in FIGS. 3C and 3D, housing 310 optionally comprises an annular recessed area 326 in which membrane 322 is held.

The hemostasis mechanism 320 is retained within the lead lumen 344 as shown in FIG. 3A. For instance, the housing 310 is a tubular member 312 made of titanium and is laser welded to the lead 300. Alternatively, other attachment methods, such as resistance welding or adhesive bonding, are used. The housing may be attached to the lead proximal to an end of the electrode. Referring to FIG. 3D, housing 310 alternatively comprises an indented portion 328 which when inserted in the distal end of the lead 300 defines a proximally facing annular shoulder 330 which meets the exterior of lead 300.

In the embodiment shown at FIG. 3B, the hemostasis mechanism comprises the terminal pin 355 which serves as a housing in which membrane 322 is held as described herein with regard to housing 310 (FIG. 3A). Suitable materials for the terminal pin 355 include, but are not limited to, those described herein with regard to housing 310.

Figure 4:
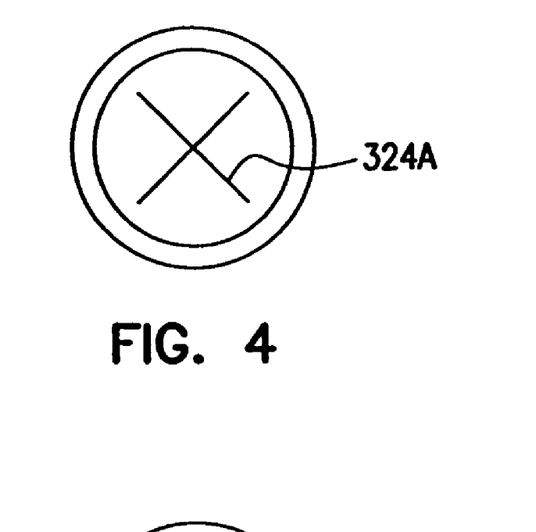
FIG. 4 is an end view of a hemostasis mechanism as shown in FIGS. 3A-3D, showing an alternative embodiment of a valve.
Figure 5:
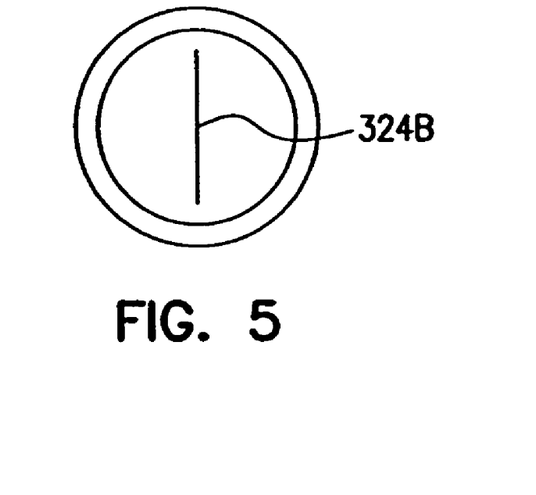
FIG. 5 is an end view of a hemostasis mechanism as shown in FIGS. 3A-3D, showing an alternative embodiment of a valve.
Figure 6:
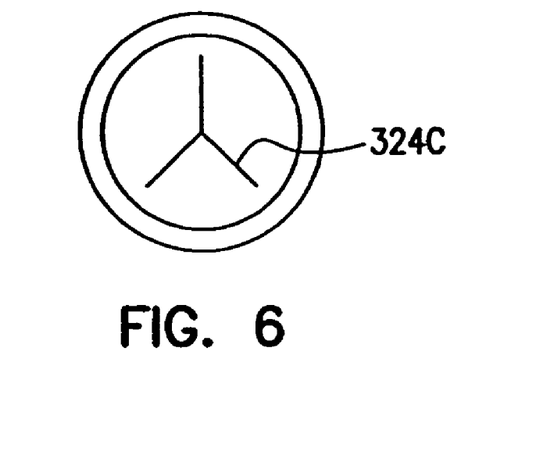
FIG. 6 is an end view of a hemostasis mechanism as shown in FIGS. 3A-3D, showing an alternative embodiment of a valve.

In one embodiment, membrane 322 comprises a cusp valve mechanism 324 which allows the passage of a needle 350 or guide wire 350 therethrough and prevents the migration of blood into the lead lumen. In one embodiment, the seal and valve are comprised of silicone rubber or other suitable biocompatible polymer. Variations for the cusp valve mechanism 324 are shown in FIGS. 4-6. FIG. 4 shows a quad cusp valve 324A. In an alternative embodiment, valve 324 is a bicusp valve, as shown at 324B of FIG. 5, or a tricusp valve as shown at 324C of FIG. 6. In further embodiments the membrane 322 shown at FIG. 3A comprises a cusp valve mechanism as shown at FIGS. 4-6. In further embodiments, the lead shown at FIG. 3B comprises a cusp valve mechanism as shown at FIGS. 4-6.

Figure 7:
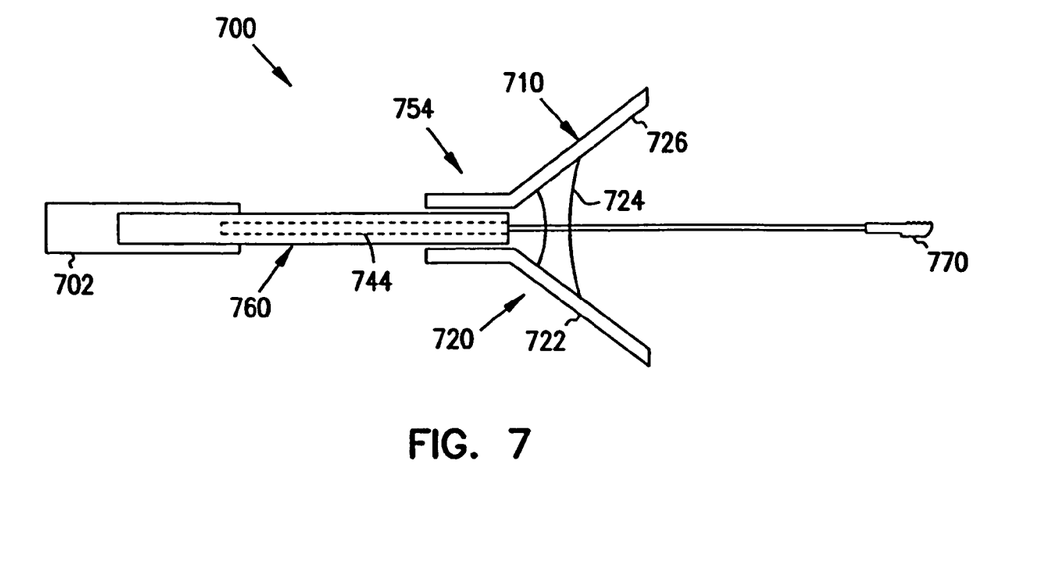
FIG. 7 is a cross-sectional view of the proximal portion of an over the wire left ventricular lead for monitoring and stimulating the heart constructed in accordance with one embodiment.

Referring to FIG. 7, a seal 720 is shown. The seal comprises a removable disposable mechanism 722 comprising a housing 710 with a membrane 724 housed therein. The housing 710 is attached to the lead body 702 at the proximal end 754 of the lead 700. The housing 710 attaches to the terminal pin 760 of the lead 700.

Figure 8:
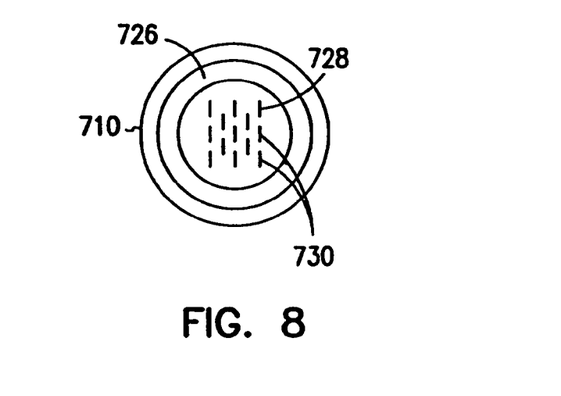
FIG. 8 is a distal end view of a lead seal as shown in FIG. 7.

The housing 710 of the seal 720 may be made of molded plastic, silicone rubber, or polyurethane. The membrane 724 is attached to and extends across the interior 726 of the housing 710. In one embodiment, membrane 724 is made of a biocompatible polymeric material, such as silicone rubber or polyurethane. In one embodiment, the membrane is integral with the housing, molded as one piece. The membrane 724 has a small hole or slit 728 (FIG. 8) to permit penetration with a needle to fill the lead lumen 744 with saline or other suitable sterile solution. Referring to FIG. 8, in one embodiment the membrane has multiple slits 730.

When the needle is withdrawn, the polymer membrane 724 closes sufficiently to maintain a hydraulic lock on the fluid in the lumen 744. The guide wire 770, optionally is passed through the membrane 724 and inserted into the lead lumen 744 and the lead 700 is deployed in the usual fashion. In a further option, the lead 700 is deployed using a catheter and/or the guide wire 770. The column of saline, maintained in the lead lumen 744 by the attached membrane 724, an optional second membrane and/or venous pressure, prevents blood from entering the lead lumen 744 and mitigates handling problems due to coagulation of blood within the lead 700.

In a method of use, a lead 700 is provided, and a seal 720 is attached to the lead 700, for example, by attaching a housing to the terminal pin 760 of lead body 702 at the proximal end of the lead. A needle is inserted in the hole or slit 728 of the seal membrane 724 to fill the lead lumen 744 with saline or other suitable sterile solution. Venous pressure maintains the column of fluid therein. The needle is withdrawn, and the polymer membrane 724 closes sufficiently to maintain a hydraulic lock on the fluid in the lumen 744. The guide wire 770 is optionally passed through the membrane 724 and inserted into the lead lumen 744. It should be noted that the guide wire 770 can be inserted into the lead lumen 744 prior to or after the filling of the lumen 744 with the sterile solution. The lead 700 is then deployed in the usual fashion. The column of saline is maintained in the lead lumen 744 by the attached membrane 724 and venous pressure and/or an additional distal seal. In one embodiment, lead 700 further comprises a distal hemostasis mechanism, as shown at FIG. 3A, and the column of saline is maintained in the lead lumen 744 between membrane 724 and the membrane of a distal hemostasis mechanism (as shown at 324 of FIG. 3A). The column of saline prevents blood from entering the lead lumen 744 and mitigates handling problems due to coagulation of blood. In an alternative embodiment, the lead is disposed in and guided within a guide catheter before, during, or after the fluid is injected into lumen 744.

Figure 9:
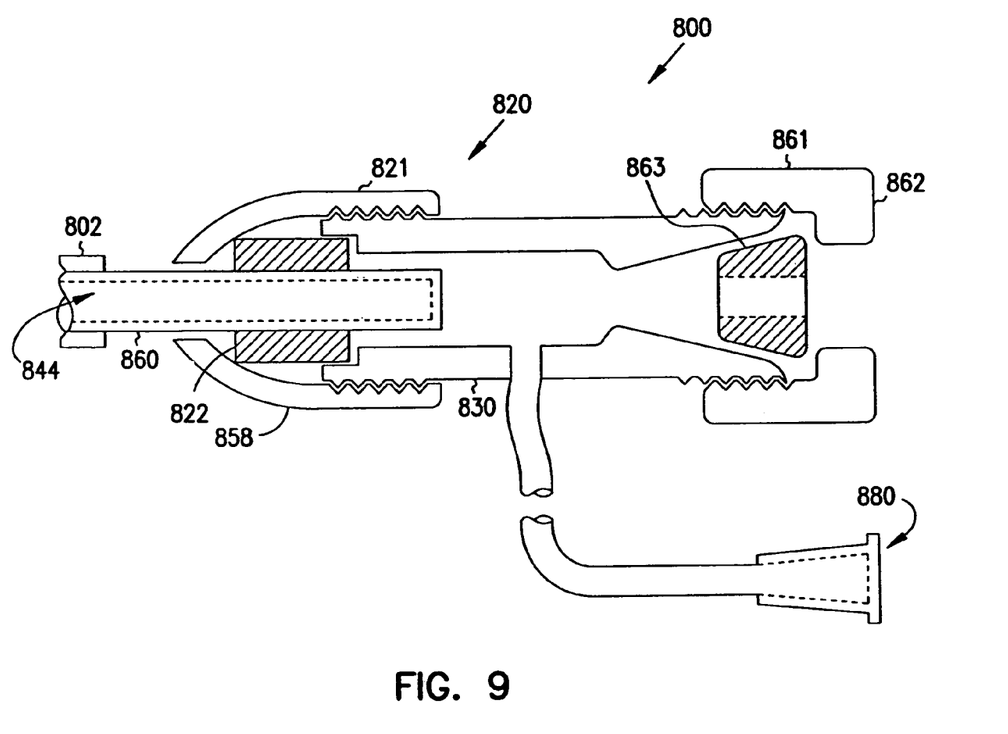
FIG. 9 is a cross-sectional view of the proximal portion of an over the wire left ventricular lead for monitoring and stimulating the heart constructed in accordance with one embodiment.

An alternative embodiment as shown in FIG. 9 is a lead 800 having a main lead body portion 802, a lumen 844 and a terminal pin 860. Seal mechanism 820 comprises two grommet style hubs 858 and 862 located at either end of body 830. Seal mechanism 820 is attached to terminal pin 860 by a grommet assembly 858. The grommet assembly 858 is comprised of locking hub 821 and elastomeric grommet 822 and attaches the seal mechanism 820 to lead terminal pin 860 and seals tightly. The hemostasis valve provides for passage of a guide wire (not shown) and is comprised of hub 861 and elastomeric grommet 863. Seal mechanism 820 further comprises a side injection port 880 for periodic or continuous introduction of sterile fluid.

It is to be understood that the above description is intended to be illustrative, and not restrictive. Many other embodiments will be apparent to those of skill in the art upon reading and understanding the above description. For instance, the seal can be used with a variety of medical devices. Such a medical device may comprise or require a first seal at its proximal end and a second seal at its distal end. Although the use of the lead has been described for use in a cardiac pacing system, the lead could as well be applied to other types of body stimulating systems. In addition, the lead could also be applicable to bipolar pacing leads having two separate conductors, and to multipolar pacing leads employing multiple conductor leads. The scope of the invention should, therefore, be determined with reference to the appended claims, along with the full scope of equivalents to which such claims are entitled.

What is claimed is:

1. An implantable lead for implantation by a guidewire on or about the heart, the lead comprising:
    a lead body having distal and proximal ends, the lead body defining a lumen extending from a distal aperture in the distal end of the lead body toward the proximal end of the lead body;
    a conductor disposed within the lead body;
    an electrode disposed proximate the distal end of the lead body, the electrode electrically coupled to the conductor; and
    a seal at the distal end of the lead body, the seal having an open and a closed state, wherein when the seal is in the open state the seal receives the guidewire therethrough and when the seal is in the closed state the seal prevents fluid from entering the lumen of the lead body;
    wherein the seal is transitionable from the open state to the closed state and is coupled to a housing having a proximally located shoulder.

2. The lead of claim 1, wherein the seal includes a cylindrical-shaped member having a closeable central aperture.

3. The lead of claim 1, wherein the seal includes a member coated with expandable matrix material.

4. The lead of claim 1, wherein at least a portion of the seal is formed from expandable matrix material.

5. The lead of claim 1, wherein the seal includes a cup-shaped member coupled with the distal end of the lead body.

6. An implantable lead for implantation by a guidewire on or about the heart, the lead comprising:
    a lead body having distal and proximal ends, the lead body defining a lumen extending from a distal aperture in the distal end of the lead body toward the proximal end of the lead body,
    a conductor disposed within the lead body;
    an electrode disposed proximate the distal end of the lead body, the electrode electrically coupled to the conductor; and
    a closable seal disposed at the distal end of the lead body and on an inner surface of the lead body, the closable seal defining a closable seal lumen for receiving the guidewire and includes at least one cusp.

7. The lead of claim 6, wherein the closable seal includes a cylindrical-shaped member.

8. The lead of claim 6, wherein the closable seal is a bicusp seal.

9. The lead of claim 6, wherein the closable seal is a tricusp seal.

10. The lead of claim 6, wherein the closable seal comprises a substantially rigid housing.

11. The lead of claim 6, wherein the closable seal is a quad cusp seal.

12. An implantable lead for implantation by means of a guidewire on or about the heart, the lead comprising:
    a lead body having distal and proximal ends, the lead body defining a lumen extending from a distal aperture in the distal end of the lead body toward the proximal end of the lead body;
    a conductor disposed within the lead body;
    an electrode disposed proximate the distal end of the lead body, the electrode electrically coupled to the conductor; and
    a seal at the proximal end of the lead body, the seal having a first state wherein the seal defines an aperture to receive the guidewire, the seal having a second state wherein the seal limits the flow of fluids into the lead body.

13. The lead of claim 12, wherein the seal aperture is adapted to close when the guidewire is removed from the aperture.

14. The lead of claim 12, wherein the seal includes at least one cusp.

15. The lead of claim 12, wherein the seal is disposed on an inner surface of the lead body.

16. The lead of claim 12, wherein the seal is coupled to a housing having a proximally located shoulder.

* * * * *